United States Patent [19]

Frey

[11] 4,206,504

[45] Jun. 3, 1980

[54] METHOD OF ANALYZING A MEASURING LIQUID AS A FUNCTION OF A PREPARATORY STATE OF A SAMPLE CONTAINED IN THE MEASURING LIQUID

[75] Inventor: Raymond Frey, Zürich, Switzerland

[73] Assignee: Contraves AG, Zürich, Switzerland

[21] Appl. No.: 10,963

[22] Filed: Feb. 9, 1979

[30] Foreign Application Priority Data

Mar. 14, 1978 [CH] Switzerland ............... 2735/78

[51] Int. Cl.² ............... G01N 33/16; G01N 21/22; G01N 27/00
[52] U.S. Cl. ............... 364/416; 324/71 CP; 364/497; 364/571
[58] Field of Search ............... 364/416, 571, 497; 324/71 CP; 356/39–42; 235/92 PC; 422/67

[56] References Cited

U.S. PATENT DOCUMENTS

| | | | |
|---|---|---|---|
| 3,973,189 | 8/1976 | Angel et al. | 364/571 X |
| 4,061,469 | 12/1977 | DuBose | 364/416 X |
| 4,093,849 | 6/1978 | Baxter, Jr. et al. | 364/416 X |
| 4,129,854 | 12/1978 | Suzuki, et al. | 364/416 X |

*Primary Examiner*—Edward J. Wise
*Attorney, Agent, or Firm*—Werner W. Kleeman

[57] ABSTRACT

Measuring devices each deliver a measuring value for a property of the measuring liquid. From certain measuring values there are formed auxiliary values. Each auxiliary value is compared with a threshold value in order to produce a recognition signal. The individual recognition signals are grouped together into a recognition-data word. Each preparatory state corresponds to a respective preparatory-data word. The calibrated state corresponds to a calibration-data word. The recognition-data word is compared with the other data words. Upon coincidence thereof, there is produced an appropriate control signal which is delivered to a computer, in order to trigger thereat a computation operation corresponding to the preparatory state or a calibration.

For instance, in a diluted blood sample there are measured the erythrocyte concentration, the hemoglobin content and the conductivity and used as auxiliary values. Depending upon the results of the comparison of such auxiliary values with the related threshold values there is produced a control signal which triggers the corresponding computation of the erythrocyte concentration or the hemoglobin content in the blood sample or the calibration of such computation.

The invention is preferably employed for hemotological analysis and more generally for the series analysis of liquids.

5 Claims, 3 Drawing Figures

METHOD OF ANALYZING A MEASURING LIQUID AS A FUNCTION OF A PREPARATORY STATE OF A SAMPLE CONTAINED IN THE MEASURING LIQUID

BACKGROUND OF THE INVENTION

The present invention relates to a new and improved method of analysing a measuring liquid in an analysis system.

More specifically, the method of the invention is of the type employing measuring devices which deliver a respective measuring value for a respective predetermined property of the measuring liquid. The measuring liquid essentially consists of a carrier liquid and a sample contained therein which is in a preparatory state, and the preparatory state constitutes one of a number or predetermined preparatory states correlated to the analysis system. At least one characteristic value of the sample is calculated in a computer from at least one of the measuring or measurement values and at least one coefficient correlated to the characteristic value and the preparatory state.

The sample is for instance a blood sample. During the examination of a blood sample it is known to measure one or more of the following characteristic values: concentration of the erythrocytes, concentration of the leucocytes, concentration of the thrombocytes, weight concentration of hemoglobin, mean volume of the erythrocytes, volume proportion of the erythrocytes in the blood sample (hemotological critical value), mean weight of the hemoglobin in an erythocyte, and possibly still other characteristic values or parameters. The sample also can consist of, for instance, other biological substances, such as urine, bile, lymph, plasma, in which there are to be determined different components such as dyes, sugar, protein and so forth as the characteristic values. It is also possible to analyse bacteria colonies, waste water samples, dust samples, in which there is to be measured the concentration of substances and/or the distribution of particles. Finally, the sample can be a placebo or a standard sample for calibration purposes.

To perform such analysis these samples are generally admixed with a carrier liquid—for instance water or isotonic plasma replacement solution—in a predetermined dilution. Depending upon the requirements, it is also possible to perform chemical or biological treatments—for instance oxidation, reduction, hemolysis and so forth—for instance fluorescence or radioactivity—by the addition of a marking substance. Such treatment of the sample, before or after its dilution in the carrier liquid, as well as the attainment of the desired solubility or suspension effect with desired dilution degree, are collectively termed the "preparation of the sample", and the state or condition in which the sample ultimately appears in the carrier liquid is designated as the "preparation or preparatory state".

Analysis systems of the previously mentioned type are known to the art, for instance, from German Pat. Nos. 1,673,146, 1,798,431, and 2,324,057. In such type analysis systems there are determined a number of characteristic values by means of a number of analysis devices. Each analysis device which is composed, among other things, of a sensor and evaluation device, is however tuned to a predetermined preparatory or preparation state, and it is not immaterial whether sample preparation has been carried out manually or, for instance, as disclosed in the aforementioned Pat. No. 1,798,431, by the device itself. Nothing is provided for an automatic determination, wherein for the purpose of calibrating this device there is analysed pure carrier liquid. Also, it is not possible to selectively employ the same analysis device for counting erythrocytes, leucocytes, or thrombocytes and thus, to save equipment costs. The analysis devices, in combination with the therewith connected computer devices, deliver false values of the characteristic values if there are employed other than the contemplated preparation states.

An analysis of the pure carrier liquid has been proposed, for instance, in the German Patent Publication No. 2,058,081. Here, in an additional analysis device there is continuously measured pure carrier liquid, in order to accommodate a coefficient used in the computation of a characteristic value to the changes in the properties of the pure carrier liquid. Notwithstanding the foregoing measures, also with this analysis system false values are produced if there are employed other preparation states than the single one which is contemplated.

Methods for determining false measuring values have been proposed, for instance, in German Pat. No. 2,116,595 and German Pat. No. 2,120,697. However, in this case one is only concerned with the determination of the faulty functioning of an analysis device. There is no correlation with the preparatory or preparation state of the sample. Moreover, the comparison of measuring values with threshold values in analysis systems is known as such. Apart from determining faulty functions such is also used for the classification of measuring values for producing a histogram, such as for instance disclosed in the published German Patent Application No. 2,418,559.

In the published German Patent Application No. 2,166,597 there has been disclosed a self-regulating determination of a characteristic value based upon the preparatory state of the sample. In this analysis system the coefficients needed for the unmistakable formation of the analysis results are automatically prepared. For this purpose there are used liquid containers provided with special coding means. A respective predetermined preparatory state corresponds to a respective code character or sign, such that the insertion of the liquid container into the analysis device sets the system to computation of a characteristic value which corresponds to the code character or sign. The analysis system is self-regulating as concerns the code sign which is carried by the liquid container, but not in respect of the liquid contained within the container. The operator must therefore make sure that, in accordance with the preparatory states, there is always used the correct liquid container. While the problem of self-regulating analysis systems was recognized in the aforementioned patent, the proposed solution cannot however be designated as self-regulating.

The self-regulation of the analysis system, as for instance proposed in the published German Patent Application No. 2,529,902, need not be limited to the selection of the suitable coefficients. Quite to the contrary, it can relate to the selection of the entire appropriate measurement and calculation program. Also in this case, the self-regulation is controlled by mechanical-optical means which are manually correlated by the operator to the liquid containers containing the samples, so that also this solution has the previously discussed drawbacks and cannot be characterized as self-accommodating or self-regulating.

SUMMARY OF THE INVENTION

Therefore, with the foregoing in mind, it is a primary object of the present invention to provide a new and improved method of analysing a measuring liquid as a function of a preparatory or preparation state of a sample contained in the measuring liquid in a manner not associated with the aforementioned drawbacks and limitations of the prior art proposals.

Another and more specific object of the present invention aims at providing, for an analysis system of the previously mentioned type, a method which enables automatically accommodating the determination of a characteristic value, in other words directly and especially without requiring the operator to do anything about the preparatory state of a sample.

Now in order to implement these and still further objects of the invention, which will become more readily apparent as the description proceeds, the proposed solution of these objects is based upon the following recognitions: during the course of the analysis there initially must be determined the preparatory state of the sample; only then is it possible to calculate the characteristic value or values; the preparatory state can be determined based upon one or a number of measuring or measurement values, and it is not necessary that there be used the same measuring values which have been employed for computation of the characteristic value or values.

For instance, the thrombocyte concentration in blood should be determined, and the preparation of the blood sample essentially resides in either diluting the blood in an isotonic plasma replacement or substitute solution in a ratio of 1:80,000 or centrifuging the blood and diluting the residually obtained plasma in an isotonic plasma replacement solution in a ratio of 1:2200. In order to determine the thrombocyte concentration there are measured the number of thrombocytes in, for instance, 200 $\mu$l of sample-containing measuring liquid and the obtained measuring value, depending upon the employed preparation, is multiplied by 400 or by 11 in order to express the desired characteristic value in a unit which is conventional in this art (number of particles per $\mu$l). It is of course known that in human blood there are normally contained 150,000 to 350,000 thrombocytes per $\mu$l; depending upon the employed preparation the measurement or measuring value normally will be in the order of magnitude of 600 or 20,000. A threshold value thus can be set at 4,000. By comparison with this threshold value it is readily possible to correlate measurement values of, for instance, 1,000 or 10,000 respectively, to one of both preparatory states, although such measuring values clearly correspond to pathological thrombocyte concentrations of 400,000 and 110,000 $\mu l^{-1}$—the alternative correlation would result in the nonprobable thrombocyte concentration of 11,000 and 4,000,000 $\mu l^{-1}$. Doubtful cases arose however with measuring values of for instance 5,000; the corresponding resulting thrombocyte concentration amounted to 2,000,000 $\mu l^{-1}$ for one of the preparatory states, in the other preparatory state to 55,000 $\mu l^{-1}$. Both of these thrombocyte concentrations are indeed markedly pathological, however both are still possible even if less probable. In this case the comparison between the measuring value and the threshold value does not enable differentiating between both possible preparatory or preparation states of the sample. There must be employed a further distinguishing characteristic, which, for instance, can be the erythrocyte concentration. A very low erythrocyte concentration can lead to the conclusion that the sample is plasma, and consequently, is present in a dilution ratio of 1:2200, whereas a measuring value of the erythrocyte count, corresponding to a physiologically attainable erythrocyte concentration, can signify that the sample is blood, and consequently, is present in a dilution ratio of 1:80,000.

Now in accordance with the aforementioned proposals the inventive method is basically manifested by the features that there are formed auxiliary values from the measuring values delivered by the selected measuring devices. Each auxiliary value is compared with a predetermined correlated threshold value, and there is produced a binary recognition signal which is correlated to the result of the comparison. The recognition signals, grouped together in a predetermined arrangement into a recognition-data word, are compared with preparation-data words prescribed for each of the possible preparatory states, and upon coincidence of the recognition-data word with a preparation-data word there is produced a logical control signal characterizing one of the corresponding preparatory states. This control signal is delivered to a computer in order to thus trigger thereat the calculation of the characteristic value which corresponds to the preparatory state designated by the control signal.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1:
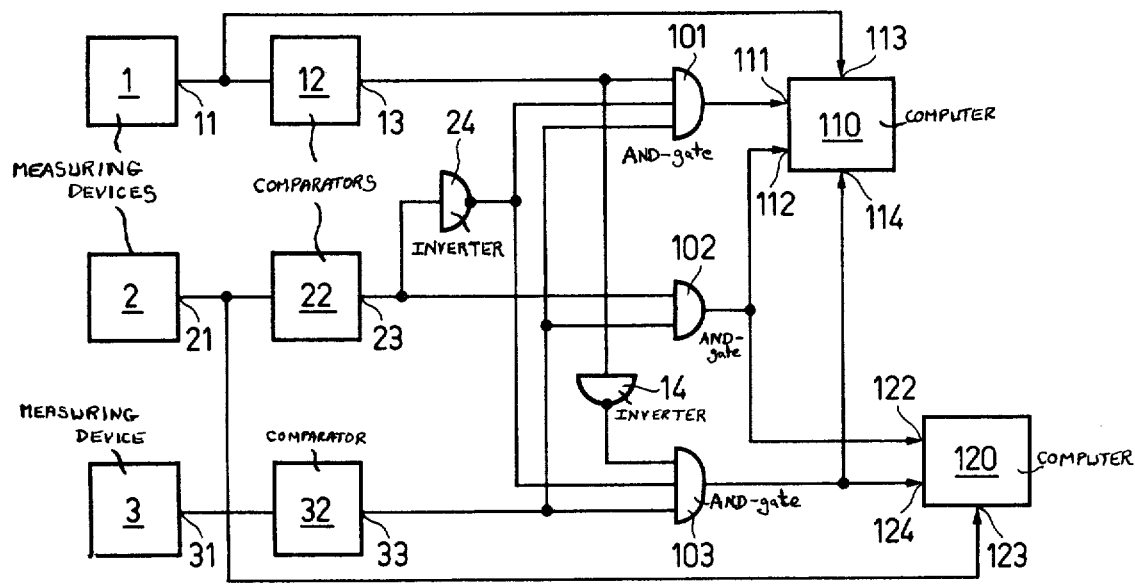
FIG. 1 is a schematic illustration of a hemotological analysis system for performance of a first exemplary embodiment of the inventive method.

Describing now the drawings, in order to explain a first exemplary embodiment of the method of the invention there has been schematically shown in FIG. 1 a hemotological analysis system. The measuring liquid to be analyzed by this system comprises, in a first preparatory or preparation state, a blood sample which has been diluted in isotonic plasma replacement solution, for instance in a solution of 0.9% sodium chloride in water, in a ratio of 1:80,000. In a second preparatory state the measuring liquid consists of a blood sample which has been diluted in isotonic plasma replacement solution in a ratio of 1:400, there having been added a hemolyzing agent, for instance trimethyl-hexadecylammonium chloride. In a calibrated state the measuring solution consists of pure isotonic plasma replacement solution. At the start of the measuring operation it is not necessary to introduce to the analysis system information as to the nature of the preparatory state or whether the calibration state is present. The analysis system determines this automatically, as will be demonstrated by the description to follow.

As to the analysis system, reference character 1 designates a measuring device for counting the particles suspended in the measuring liquid. Such measuring device 1 may be, for instance, a particle counter of the type described in the German Pat. No. 2,121,201, the disclosure of which is incorporated herein by reference, which is structured to count both the erythrocytes and leucocytes. At an output 11 of the particle counter 1 there is delivered a measuring or measurement value formed from a digital counter result.

Reference character 2 designates a measuring device for the photometric measurement of the hemoglobin content in the measuring liquid. The measuring device 2 may be, for instance, a photometer of the type described in German Pat. No. 2,535,128, the disclosure of which is incorporated herein by reference, which is structured for the determination of the total content of the measuring liquid of different hemoglobin derivatives, for instance Hb, $HbO_2$, HbCO and Hi. At an output 21 of the photometer 2 there is delivered a measuring value which corresponds to the concentration of the present hemoglobin and either can appear in digital or analog form.

Reference character 3 designates a measuring device for measuring the conductivity of the measuring liquid. Such measuring device 3 may be of the type described, by way of example, in the U.S. Pat. No. 2,871,445, the disclosure of which is likewise incorporated herein by reference. At an output 31 of the conductivity measuring device 3 there is delivered a measuring value which corresponds to the conductivity of the measuring liquid and either is present in digital or analog form.

The measuring or measurement values are delivered from the outputs 11, 21 and 31, by the corresponding measuring devices 1, 2 and 3, respectively, by means of related lines or conductors to a respective comparator 12, 22 and 32. In each such comparator 12, 22 and 32 the infed measuring value is compared with an associated and predetermined threshold value which is set equal to 10% of the lower threshold of the measuring or measurement value which is to be expected for human blood. As is known in the case of human blood, the erythrocyte concentration is in the order of between 4,000,000 and 6,000,000 particles per $\mu l$, the leucocyte concentration approximately between 5,000 and 11,000 particles per $\mu l$, the hemoglobin concentration approximately between 120 and 180 g/l, whereas the specific conductivity of the conventionally employed isotonic plasma replacement solution, used as carrier liquid in both preparatory states and in the calibration state, amounts to about 1.5 and 2 $ohm^{-1}.m^{-1}$. Consequently, the threshold value of the comparator 12 is set equal to the measuring value which is delivered by the measuring device 1 when such would measure a measuring liquid containing 5 particles per $\mu l$ (first preparatory state). The threshold value of the comparator 22 is set equal to the measuring value which is delivered by the measuring device 2 when such would measure a measuring liquid containing 30 mg/l hemoglobin (second preparatory state). Finally, the threshold value of the comparator 32 is set equal to the measuring value which is delivered by the measuring device 3 when such would measure a measuring liquid having a specific conductivity of 0.15 $ohm^{-1}.m^{-1}$ (this precludes among other things cleaning liquid). Such type comparators for the comparison of an infed variable measuring value with a predetermined threshold value are known to the art, and specifically, for digital as well as for analog values, and therefore, need not be here further considered. At each respective output 13, 23, 33 of the comparators 12, 22 and 32 there appears a respective logical signal, which assumes the logical state "1" when the measuring value is greater than the threshold value and, in the opposite case, assumes the logical state "0".

By means of suitable signal lines or conductors the signals from the outputs 13, 23 and 33 are fed to the input side of an AND-gate circuit 101, and for the logical reversal or inversion of the signal from the output 23 this signal is delivered by means of an inverter 24. An AND-gate circuit 102 has delivered by means of suitable lines or conductors, at the input side thereof, the signals emanating from the outputs 23 and 33. By means of suitable lines or conductors the signals from the outputs 13, 23 and 33 are delivered to the input side of an AND-gate circuit 103, and for the logical reveral or inversion of the signals from the outputs 13 and 23 the first of these signals is delivered by means of an inverter 14 and the second of these signals by means of the inverter 24.

The measuring or measurement value from the output 11 of the measuring device 1 is infed to the data input 113 of a digital computer 110 by means of an appropriate line or conductor. The output signals of the AND-gate circuits 101 and 102 are infed to a respective control input 111 and 112 of the computer 110 by means of appropriate lines or conductors. The measuring value from the output 21 of the measuring device 2 is infed by means of an appropriate line to a data input 123 of a computer 120. Depending upon the nature of the measuring value appearing at the output 21, the computer 120 is either a digital or analog computer; in the case of an analog measuring or measurement value it also can be a digital computer which is provided with an analog-digital converter for converting the measurement value into digital form. The output signal of the AND-gate circuit 102 is infed, by means of a related line, to a control input 122 of the computer 120. Finally, the output signal of the AND-gate circuit 103 is infed to a respective control input 114 and 124 of the computers 110 and 120, respectively, by means of corresponding lines or conductors.

The analysis system described in conjunction with FIG. 1 renders possible performance of the following measuring method course or procedures: initially the measuring liquid to be analysed is simultaneously infed to the three measuring devices 1, 2 and 3, whereafter there appear at the outputs 11, 21 and 31 of such measuring devices 1, 2, and 3 the measuring or measurement values. In the event that the measuring liquid is successively infed into the three measuring devices 1, 2 and 3, then there are to be provided for instance at the outputs 11, 21 and 31 intermediate storages which, in conventional manner, are reset prior to the start of the analysis and during analysis store and hold the measuring values. The measuring value at the output 11 serves as the first auxiliary value, the measuring value at the output 21 serves as the second auxiliary value, the measuring value at the output 31 serves as the calibration-auxiliary value. In the comparators 12, 22, 32 these auxiliary values are compared with the correlated threshold values. The logical signal which appears, as a result of the comparison, at the output 13 of the comparator 12 serves as a corresponding first recognition signal. The logical signal which appears, as a result of the comparison, at the output 23 of the comparator 22 serves as the corresponding second recognition signal. Finally, the logical signal which appears, as a result of the comparison, at the output 33 of the comparator 32 serves as the corresponding calibration signal.

As is well known in the electronics art, the AND-gate circuits 101, 102 and 103 deliver a logical output signal "1" when there appear at all of their inputs a respective logical signal "1". These AND-gates circuits 101, 102 and 103 thus serve as comparators between a reference state 1, 1, 1, and the combination of the momentary actual states delivered to their inputs.

Due to the workings of the inverter 24 the AND-gate circuit 101 delivers an output signal "1" when at the same time there appears at the output 13 a first recognition signal having an actual state "1", at the output 23 a second recognition signal having an actual state "0", and at the output 33 a calibration signal having an actual state "1". Consequently, the action of this combination of the inverter 24, the AND-gate circuit 101 and the corresponding lines or connections, is to group together the first recognition signal, the second recognition signal and the calibration signal, in this sequence, into a recognition-data word, to compare such with a first preparation-data word 1, 0, 1 (corresponding to the same sequence), and upon coincidence to deliver a first logic control signal "1" to the input 111 of the computer 110. In similar fashion, the action of the AND-gate circuit 102 and the corresponding lines or connections is to form the same recognition-data word, to respectively compare such with one of the second preparation-data words, 1, 1, 1 or 0, 1, 1, and upon coincidence with one of such preparation-data words to infeed a second logic control signal "1" to the inputs 112 and 122 of the computers 110 and 120, respectively. In similar manner, the function of the AND-gate circuit 103 and the corresponding lines or connections is to compare the same recognition-data word with a calibration-data word 0, 0, 1, and upon coincidence to infeed a logic control signal "1", designating the calibration operation, to the inputs 114 and 124 of the computers 110 and 120 respectively.

As will be readily apparent, the appearance of the first control signal means that in the measuring liquid there are present many particles and high conductivity, however little hemoglobin. This thus corresponds to the first preparatory state (blood dilution, 1:80,000). The appearance of the second control signal means that there is present a great deal of hemoglobin and high conductivity (the number of particles is optional); this thus corresponds to the second preparatory state (blood dilution 1:400 with hemolysis). The appearance of the control signal designating the calibration operation means that there are present few particles and little hemoglobin, but however high conductivity; this thus corresponds to the calibration state where the measuring liquid consists of pure isotonic plasma replacement solution.

The computer 110 is constructed or programmed in a manner which is known or obvious to the person skilled in the art for performing the following functions. Initially there is performed the calibration operation. Upon obtaining the control signal at the control input 114 and corresponding to the calibration operation, there is stored the measuring value, as a rule predicated upon contaminants, which is obtained at the data input 113, in order to be subtracted as a base value from later obtained measuring values corresponding to the blood samples. Upon obtaining the first control signal at the control input 111 there is subtracted from the measuring value obtained at the data input 113 the stored base value. Thereafter, the obtained difference is multiplied by a coefficient which corresponds to the operation of the measuring device 1 and the dilution ratio 1:80,000, and the result of the particle counting is converted into number of particles per $\mu$l. The result, expressed in such unit, is then visually displayed or printed. Upon obtaining the second control signal at the control input 112 there is accomplished the same procedure, with the difference that the coefficient now corresponds to the dilution ratio 1:400.

The computer 120 is likewise constructed or programmed in a manner familiar to those skilled in the art for performing the following functions. Upon obtaining the control signal at the control input 124, designating the calibration operation, there is stored the measuring value obtained at the data input 123, in order to be subtracted as a base value from later obtained measuring or measurement values corresponding to the blood samples. Upon obtaining the second control signal at the control input 122 there is subtracted the stored base value from the measuring value obtained at the data input 123. Thereafter, the obtained difference is multiplied by a coefficient which corresponds to the operation of the measuring device 2 and the dilution ratio 1:400 and the result of the hemoglobin measurement is converted into g/l blood. The result, which is expressed in this unit, is then visually displayed or printed.

With the first preparatory or preparation state all of the particles are counted, so that there is indicated as the result the sum of the concentration of erythrocytes and leucocytes in the blood. Since, however, the number of leucocytes is in a ratio of about 1:1000 to the number of erythrocytes, the thus resulting system measuring error is negligible. During the second preparatory state the erythrocytes are hemolyzed, so that such system measuring error does not arise; there are only counted the leucocytes.

The described method also can be carried out with other equipment. As to the different possibilities, it is here mentioned that both of the computers 110 and 120 can be grouped together into a single computer unit or device which also encompasses the AND-gate circuits 101, 102 and 103 and the inverters 14, 24 or their functions. If the measuring or measurement values at the outputs 11, 21 and 31 all are present in digital form, then it is also possible to carry out, in the computer device, the functions of the comparators 12, 22, 32, so that the three measuring values can be directly infed to an appropriately programmed computer device. The method is then carried out in this computer device.

Figure 2:
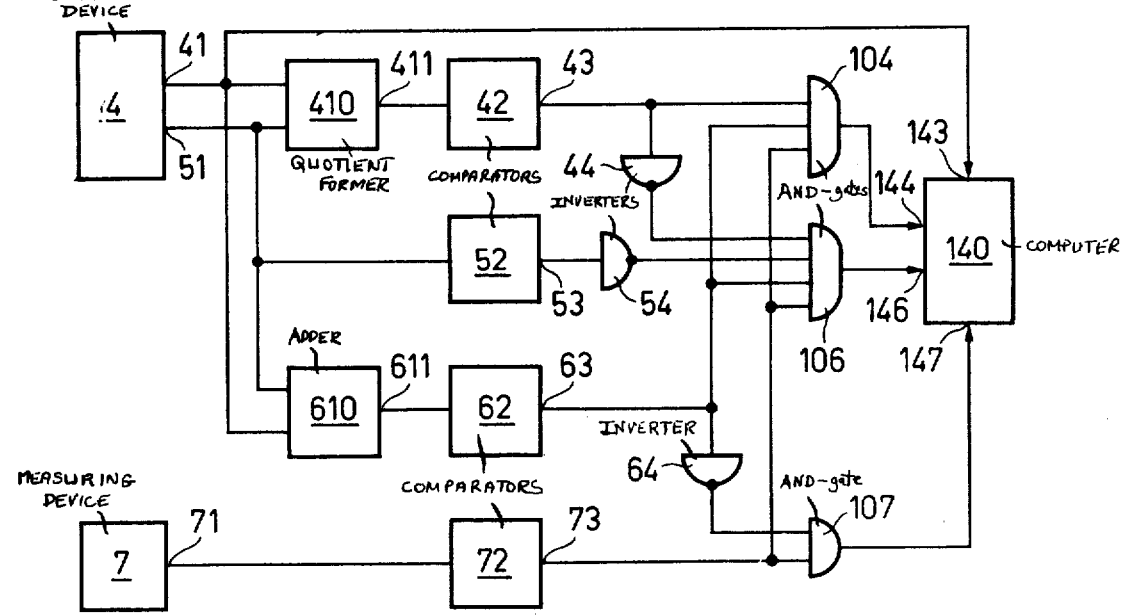
FIG. 2 schematically illustrates another hemotological analysis system for performance of a second exemplary embodiment of the method.

In order to explain a second embodiment of the method there has been schematically illustrated in FIG. 2. a hemotylogical analysis system for thrombocyte counting. The measuring liquid which is to be analysed by this system, in a first preparatory state, consists of a blood sample which has been diluted in isotonic plasma replacement solution in a ratio of 1:80,000. According to a second preparatory state the measuring liquid consists of a blood sample from which there has initially been obtained, by centrifuging, a plasma having low erythrocyte content and which subsequently is diluted in isotonic plasma replacement solution in a ratio of 1:2200. In a calibrated state the measuring liquid consists of pure isotonic plasma replacement solution. The problem to be solved of determining the prevailing preparatory state has already been previously explained.

In this analysis system reference character 4 designates a measuring device for the analysis of the particles suspended in the measuring liquid as to their classification according to size and number per size classification. Such measuring device 4 comprises, for instance, a particle analyser having a measuring cell or head of the type described in German Pat. No. 2,121,201, the disclosure of which is incorporated here by reference, and a conventional multi-channel pulse amplitude analyser which is here operated as a dual-channel analyser. At the output 41 there is delivered a measuring or measurement value corresponding to the number of thrombocytes in the measuring liquid. At the output 51 there is delivered a measuring or measurement value which corresponds to the number of erythrocytes in the measuring liquid. Both measuring values are present in the form of digital counter results.

Reference character 7 designates a measuring device for measuring the conductivity of the measuring liquid. This measuring device 7 may be, for instance, of the type described in U.S. Pat. No. 2,871,445, the disclosure of which is incorporated herein by reference. At an output 71 of this conductivity-measuring device 7 there is delivered a measuring value which corresponds to the conductivity of the measuring liquid and either is present in digital form or analog form.

The measuring or measurement values are delivered, on the one hand, from the outputs 41 and 51 by the measuring device 4 to a quotient former 410 and, on the other hand, to an adder 610 by means of appropriate lines or conductors. At an output 411 of the quotient former 410 there is delivered a digital quotient signal which is equal to the ratio of the measurement value for erythrocytes and the measurement value for thrombocytes. At an output 611 of the adder 610 there is delivered a digital summation value or signal which is equal to the sum of the measurement value for erythrocytes and the measurement value for thrombocytes.

By means of the outputs 411, 51, 611 there are delivered to a respective comparator 42, 52 and 62 the quotient of the measurement value for erythrocytes and the summation value by means of appropriate lines. In each such comparator 42, 52 and 62 there is compared the infed value with a related and predetermined threshold value. The threshold value of the comparator 42 is set to be equal to 1 (= 10% of the lower threshold of the value to be expected for human blood). As to the threshold value of the comparator 52 there is to be taken into account that also in plasma having low content of erythrocytes, there are contained approximately 10,000 to 30,000 residual erythrocytes per $\mu l$; with the first preparation state the lower threshold of the erythrocyte concentration in the measuring liquid thus is at about 50 particles per $\mu l$, with the second preparation state the upper threshold of the erythrocyte concentration is at about 15 particles per $\mu l$, so that the threshold value of the comparator 52 can be set equal to the measurement value for the number of erythrocytes which is delivered by the corresponding output 51 of the measuring device 4 when such would measure a measuring liquid containing 30 particles per $\mu l$. The threshold value of the comparator 62 is set as low as possible, and the lower threshold or boundary is governed by the concentration of the disturbing particles floating in the pure carrier liquid. A realistic threshold value is 5 particles per $\mu l$ measuring liquid. The measuring value for the conductivity is delivered from the output 71 by means of an appropriate line to a comparator 72 where this measuring value is compared with a related and predetermined threshold value which can be set equal to the measuring or measurement value for a measuring liquid having a specific conductivity of $0.15$ ohms$^{-1}$.m$^{-1}$, as already explained in conjunction with FIG. 1.

At a respective output 43, 53, 63, 73 of the comparators 42, 52, 62, 72, respectively, there appears a respective logic signal which assumes the logic state "1" when the value delivered to the related comparator from the outputs 411, 51, 611, 71 is larger than the threshold value, and, in the converse situation, assumes the logic state "0".

An AND-gate circuit 104 has infed to the input side thereof, by means of appropriate lines, the signals from the outputs 43, 63, 73. An AND-gate circuit 106 has infed thereto at its input side, by means appropriate lines, the signals from the ouputs 43, 53, 63, 73. For the logical inversion of these signals from the outputs 43 and 53 these signals are delivered by means of a respective inverter 44 and 54. An AND-gate circuit 107 has delivered thereto, by means of appropriate infeed lines, at its input side the signals from the outputs 63, 73, and for the logical inversion of the signal delivered from the output 63 such signal is infed by means of an inverter 64. The measuring or measurement value from the output 41 of the measuring device 4 is infed by means of an appropriate line to a data input 143 of a digital computer 140. The output signals of the AND-gate circuits or AND-gating 104, 106, 107 are delivered by means of appropriate lines to a respective control input 144, 146, 147 of the computer 140.

The analysis system described in conjunction with FIG. 2 allows accomplishment of the following method course or procedures. Initially the measuring liquid to be analysed is simultaneously infed to the two measuring devices 4 and 7, whereafter there appear at the outputs 41, 51 and 71 of such measuring devices the measuring or measurement values. In the event that the measuring liquid is delivered in succession to both measuring devices, then, for instance, intermediate storages are to be provided at the outputs 41, 51 71 which, in standard fashion, are reset at the start of the analysis and during the analysis store and hold the measuring values. The quotient formed in the quotient former 410 of the measuring value at the output 51 to the measuring value at the output 41, serves as the first auxiliary value, the measuring value at the output 51 serves as the second auxiliary value, the summation value of the measuring or measurement values at the outputs 41 and 51 formed at the adder or summing device 610 serves as the third auxiliary value, the measuring value at the output 71 serves as the calibration-auxiliary value. These auxiliary values are compared in the comparators 42, 52, 62, 72 with the related threshold values. The logical signal which appears, as a result of the comparison, at the output 43 of the comparator 42 serves as the corresponding first recognition signal. The logical signal which appears, as a result of the comparison at the output 53 of the comparator 52, serves as the corresponding second recognition signal. The logical signal which appears, as a result of the comparison, at the output 63 of the comparator 62, serves as the corresponding third recognition signal. Finally, the logical signal which appears, as a result of the comparison, at the output 73 of the comparator 72, serves as the corresponding calibration signal.

As has been described already in conjunction with FIG. 1, the action of the AND-gate circuit 104 and the corresponding lines or connections, is to group together the first recognition signal, the second recognition signal, the third recognition signal and the calibration signal, in this sequence, into a recognition-data word, to compare such with a respective one of the first preparation-data words 1, 0, 1, 1, and 1, 1, 1, 1 (corresponding to the same sequence), and upon coincidence with one of these preparation-data words to deliver a first logic control signal "1" to the input 144 of the computer 140. In similar manner, the action of the combination of the AND-gate circuit 106, the inverters 44 and 54 and the corresponding lines or connections, is to form the same recognition-data word, to compare such with a second preparation-data word 0, 0, 1, 1, and upon coincidence to deliver a second logic control signal "1" to the input 146 of the computer 140. In similar fashion, the action of the combination of the AND-gate circuit 107, the inverter 64 and the corresponding connections or lines, is to compare the same recognition-data word with a respective one of the calibration-data words 1, 1, 0, 1 or 0, 1, 0, 1 or 1, 0, 0, 1 or 0, 0, 0, 1, and upon coincidence with one of these calibration-data words to deliver a logic control signal "1", designating the calibration operation, to the input 147 of the computer 140.

As will be readily apparent, the appearance of the first control signal signifies that in the measuring liquid the ratio of the number of erythrocytes to the number of thrombocytes is rather large, there is present a minimum number of particles, and the conductivity is considerable, whereas the number of erythrocytes can be random. This thus corresponds to the first preparatory or preparation state (blood dilution 1:80,000). The appearance of the second control signal means that, both the ratio of the number of erythrocytes to the number of thrombocytes and also the number of erythrocytes is rather small, however, there is present at least a minimum number of particles and the conductivity is considerable. This thus corresponds to the second preparatory state (centrifuging of the blood sample and dilution 1:2200 of the remaining plasma). The appearance of the control signal, designating the calibration operation, means that there is not present any sufficient number of particles in the measuring liquid, however, there is present high conductivity. The ratio of the number of erythrocytes to the number of thrombocytes and the number of erythrocytes can be random. This thus corresponds to the calibration state where the measuring liquid consists of pure isotonic plasma replacement solution.

The computer 140 is constructed or programmed in a manner apparent to one skilled in the art for the purpose of performing the following functions. Upon obtaining a control signal at the control input 147, designating the calibration operation, there is stored the measuring or measurement value obtained at the data input 143 in order to be subtracted as a base value at a later time from the measuring values corresponding to the blood samples. Upon obtaining the first control signal at the control input 144 the stored base value is subtracted from the measuring value obtained at the data input 143, whereafter the obtained difference is multiplied by a coefficient which corresponds to the operation of the measuring device 404 and the dilution ration 1:80,000. The result of the particle counting is converted in the channel of the measuring device 4 which corresponds to the thrombocytes, into the number of particles per $\mu l$ blood. The result which is expressed in this unit is then visually displayed or printed-out. Upon obtaining the second control signal at the control input 146 there is accomplished the same procedure, with the difference that the coefficient now corresponds to the dilution ratio 1:2200.

The described method also can be carried out with other devices or equipment. Other possibilities which can be utilized is to group together into a single computer unit or device the computer 140, the AND-gate circuits 104, 106, 107 and the inverters 44, 54. This single computer device then carries out the functions of these individual components. If the measuring or measurement values at the outputs 41, 51, 71 are all in digital form, then it is also possible to carry out in the computer unit the functions of the comparators 42, 52, 62, 72 at the quotient former 410 and the adder 610, so that the three measuring values can be directly delivered to an appropirately programmed computer unit. The method then is carried out in this computer unit.

Figure 3:
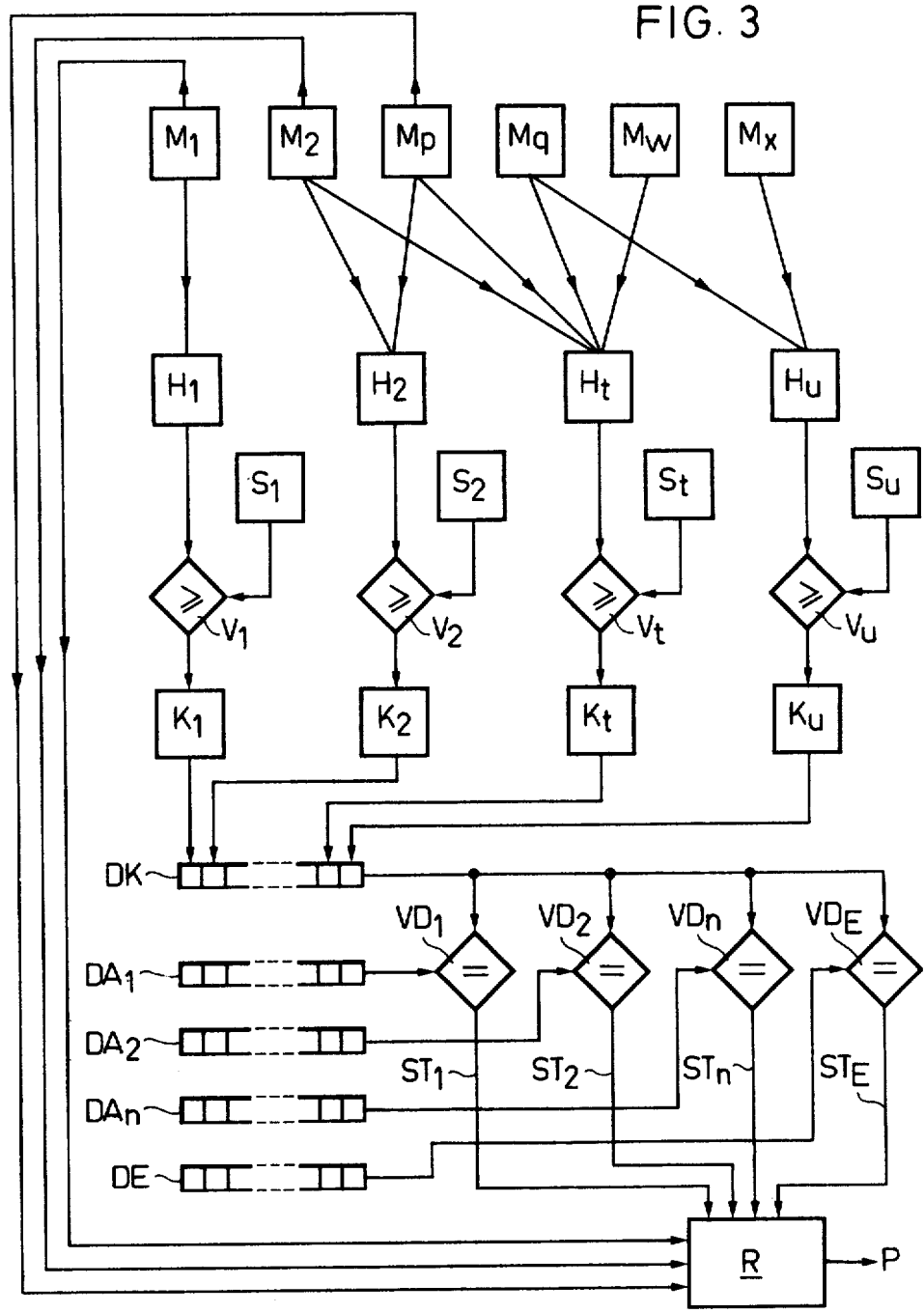
FIG. 3 schematically illustrates a generalized form of the course of the method in block circuit diagram.

A generalized form of the course of the method has been schematically illustrated in FIG. 3. There is to be calculated at least one characteristic value P from predetermined combinations of measuring values $M_1$, $M_2$ . . . $M_p$ while utilizing suitable coefficients a, b . . . g, h. Further, there is to be distinguished between a number of predetermined possible preparatory states $A_1$, $A_2$ . . . $A_n$ and a calibration state E. For instance, for the first preparatory or preparation state there is valid $P=a.M_1+b.M_2$, for the second preparatory state $P=h.M_p$, whereas P in the calibration state assumes a predetermined value $P=P_E$. The unambiguous differentiation between the preparatory states is only possible by resorting to additional measuring values $m_q$ . . . $M_w$, whereas the differentiation between the calibration procedure and a cleaning of the measuring devices requires resorting to a further measurement value $M_x$. Thus, as schematically illustrated in FIG. 3, there are measured the measuring or measurement values $M_1$ . . . $M_x$. The measurement values $M_1$ . . . $M_p$ are delivered to a computer R, in order to be processed therein into a value of the characteristic value P. The measuring values $M_1$ . . . $M_x$ are mutually combined in suitable manner for forming auxiliary values $H_1$, $H_2$ . . . $H_t$, $H_u$. As an example there has been illustrated that the value $H_1$ has been derived from $M_1$, the value $H_2$ from $M_2$ and $M_p$, the value $H_t$ from $M_2$, $M_p$, $M_q$ and $M_w$, and finally, the value $H_u$ from $M_q$ and $M_x$ (there is valid for instance $H_1=M_1$, and $H_2=M_2/M_p$, $H_t=M_2+M_p+M_q+M_w$ and $H_u=(M_q-M_x)/M_x$).

Each auxiliary value $H_1$, $H_2$ . . . $H_t$, $H_u$ has correlated thereto a predetermined threshold value $S_1$, $S_2$ . . . $S_t$, $S_u$. In the description to follow there will be explained how the threshold values are to be set. Between each auxiliary value and the related threshold value there is accomplished a respective comparison $V_1$, $V_2$ . . . $V_t$, $V_u$. As the result of the comparison there is produced a respective correlated recognition signal $K_1$, $H_2$ . . . $K_t$, $K_u$ which, for instance, assumes the actual state "1" when the auxiliary value exceeds the threshold value, and in the converse situation assumes the actual state "0". The actual states of the recognition signals $K_1$, $K_2$ . . . $K_t$, $K_u$ are then grouped together in a predetermined arrangement or sequence, for instance in the sequence of the indexes, 1, 2 . . . t, u into a data word which serves as the recognition-data word DK. In the same arrangement or sequence there are grouped together for each of the possible preparation states and for the predetermined reference states, corresponding to the calibration state, the recognition signals into a data word which serves as the momentary preparation-data word $DA_1$, DA$_2$ ... DA$_n$ as well as DE, wherein DE is correlated to the calibration state; there will be explained hereinafter how the reference values are set.

In order to determine the threshold values and the reference states, it is assumed that there is known the nature of the sample which is to be analysed, for instance, human blood, waste water from purification installations and so forth, so that it is also known what properties of the sample always appear within a given range and lie, with a predetermined variation coefficient, about a given mean value, and for which characteristics or properties this does not hold true. For instance, it is known that in the case of human blood there are present approximately 4 to 6 million erythrocytes per $\mu$l and approximately 120 to 180 g/l hemoglobin, whereas the concentration of the thrombocytes generally is in the order of between 150,000 and 350,000 per $\mu$l, however also can drop to almost null. It is also known that the specific conductivity of conventional plasma replacement solution generally in in the order of between 1.5 and 2 ohm$^{-1}$.m$^{-1}$. To form auxiliary values there are thus employed only those measurement values whose magnitude is known, based upon the properties of the samples and based upon the individual possible preparation states. For a given type of samples for instance human blood, there is decided which auxiliary values, formed in each case from a predetermined combination of measurement values, fall into magnitudes which can be properly distinguished from one another, depending upon whether the sample is in one or the other of the preparatory or preparation states or a calibration state. For istance, it will be apparent from the foregoing discussion that in a blood sample which has been diluted 1:80,000, there are present approximately 50 to 75 erythrocytes per $\mu$l, whereas in a plasma, obtained by centrifuging blood, after a dilution of 1:200 there are contained at most approximately 15 erythrocytes per $\mu$l. To distinguish between both of these preparatory states there thus can be employed as the auxiliary value the measurement value for the number of erythrocytes, and the correlated threshold value is then set equal to the measurement value, which corresponds to a measuring liquid having between 15 and 50 particles per $\mu$l, more advantageously a measuring liquid approximately in the center of this range, in other words having 30 particles per $\mu$l. More generally, each auxiliary value is correlated to one such threshold value which divides the preparation state and the calibration state unambiguously into two classes; the one class contains preparation states and possibly the calibration state, where the auxilliary value is clearly larger than the threshold value; the other class contains the remaining states; no auxiliary value is situated so close to the threshold value that the correlation of the states to the classes is associated with uncertainty. Numerical examples have already been previously given above.

The reference states of the recognition signals are in each case equal to those of the actual states of the same recognition signals which are obtained when a measuring liquid is analysed which either corresponds to the calibration state or one of the predetermined possible preparation states of a standard sample defined hereinafter. Stated in another way: in each case one of the preparation-data words DA$_1$, DA$_2$ ... DA$_n$, DE, is equal to the recognition-data word which is obtained during the analysis of a measuring liquid when this measuring liquid either contains a standard sample in a respective one of the predetermined possible preparation states A$_1$, A$_2$ ... A$_n$ or is present in the calibration state E. In this case as the normal or standard sample there is to be understood such a hypothetical sample wherein, each property which is resorted to by means of measurement values for forming the auxiliary values, is equal to the statistical mean value for the related property. Properties or measurement values which are not employed for forming auxiliary values are here not of importance. For instance, a standard sample of blood contains per $\mu$l 5 million erythrocytes, of which after hemolysis there remain exactly 20,000 erythrocytes, and in which there is contained a total of 150 $\mu$g hemoglobin and 250,000 thrombocytes. A standard carrier liquid has a specific conductivity of 1.75 ohms$^{-1}$.m$^{-1}$, it does not contain any hemoglobin, however 1 particle per $\mu$l. Of course, it is not necessary to determine the reference states by measurement of a standard sample. For the determination of the reference states there is sufficient knowledge of the analysis system, the properties of the hypothetical standard sample and the set threshold values.

In the final analysis each preparation-data word and the calibration-data word unambiguously designates only one preparation state or the calibration state. However, it can happen that in certain ones of these words one or a number of the reference states can assume a random logical state "1" or "0", which, however, does not impair the unambiguousness of the designation. With the example described in conjunction with FIG. 2, the calibration-data word appears as x, x, 0, 1 with x equal to 1 or 0. During the further course of the method there is compared the recognition-data word DK with each preparation-data word DA$_1$, DA$_2$ ... DA$_n$ and with the calibration-data word DE. Each of these comparisons VD$_1$, VD$_2$ ... VD$_n$, VD$_E$ thus corresponds, upon coincidence, to a respective logical control signal ST$_1$, ST$_2$ ... ST$_n$, ST$_e$, which designates the corresponding preparatory state. From the foregoing discussion it should be apparent that, the coincidence of the recognition-data word with one of the preparation-data words or with the calibration-data word precludes coincidence with the other words, so that at any time there only can be produced one of the control signals ST$_1$, ST$_2$ ... ST$_n$, ST$_E$. This control signal is then delivered to the computer R, in order to calculate therein the characteristic value P from the infed measurement values M$_1$, M$_2$ ... M$_P$ while utilizing the suitable coefficients from the list a, b ... g, h; for instance the control signal ST$_1$ triggers the computation of P according to the equation $P = a.M_1 + b.M_2$, whereas the control signal ST$_2$ triggers the calculation of P according to the equation $P = h.M_P$. Of course, there also could be calculated other characteristic values from a respective predetermined combination of measurement values and coefficients, as has been already described for instance in conjunction with FIG. 1 for the second preparatory state. The control signal ST$_E$, designating the calibration operation, triggers in the computer a special computation wherein the appropriate coefficients, from the list a, b ... g, h, are set to the suitable value, in order to bring the characteristic value P to the calibration value $P = P_E$. In conjunction with FIG. 1 and FIG. 2 this calibration value P$_E$ has been designated as the base value. The corresponding construction or programming of the computer R will be apparent to the persons skilled in the art, and therefore need not here be further described.

With the disclosed method there is obtained the result that an analysis system is controlled so as to be self-accommodating or self-regulating in such a fashion that, the computation of the characteristic value or characteristic values of a sample to be analysed can be calibrated without the necessity for an operator interceding and there can be correspondingly carried out the preparation state of the sample. If the sample is present in one of the contemplated possible preparatory or preparation states then all operating errors are completely eliminated.

While there are shown and described present preferred embodiments of the invention, it is to be distinctly understood that the invention is not limited thereto, but may be otherwise variously embodied and practiced within the scope of the following claims.

Accordingly, what I claim is:

1. In a method of analysing a measuring liquid in an analysis system equipped with measuring devices for delivering a respective measuring value for a respective property of the measuring liquid, the measuring liquid essentially comprising a carrier liquid and a sample contained therein in a preparatory state and the preparatory state comprises one of a number of predetermined preparatory states correlated with the analysis system, and at least one characteristic value of the sample is calculated in a computer from at least one of the measuring values and at least one coefficient correlated with the characteristic value and the preparatory state, the improvement which comprises the steps of:
    forming auxiliary values from the measuring values delivered by selected ones of the measuring devices;
    comparing each auxiliary value with a predetermined correlated threshold value to obtain a comparison result;
    forming from each comparison result a binary recognition signal correlated with the comparison result;
    grouping together the recognition signals in a predetermined arrangement into a recognition-data word;
    comparing the recognition signals with preparation-data words prescribed for each of the possible preparatory states;
    upon coincidence of the recognition-data word with a preparation-data word producing a logical control signal characteristic of the corresponding preparatory state; and delivering this control signal to the computer in order to trigger therein calculation of the characteristic value which corresponds to the preparatory state characterized by the control signal.

2. The method as defined in claim 1 for the analysis of blood in an analysis system, further comprising the steps of:
    providing at least one measuring device for counting particles suspended in the measuring liquid and a measuring device for the photometric measurement of the hemoglobin content in the measuring liquid;
    the measuring liquid essentially comprising an isotonic plasma replacement solution and a blood sample contained therein in one of two preparatory states, wherein of these two preparatory states the first constitutes a higher dilution of the blood sample in the solution and the second a lower dilution of the blood sample in the solution while adding a hemolysis agent;
    equating a first of said auxiliary values to the result of the particle count and a second of said auxiliary values to the result of the photometric measurement;
    comparing the first auxiliary value with a correlated first threshold value which is predetermined in a range of 5% to 50% of the result of the particle count to be expected with a physiologically normal blood sample in the first preparatory state;
    producing as one of the recognition signals a first recognition signal having the logical state "1" or "0", depending upon whether the first auxiliary value is greater or smaller than the first threshold value;
    comparing the second auxiliary value with a correlated second threshold value which is predetermined in a range of 5% to 50% of the result of the photometric measurement which is to be expected with a physiologically normal blood sample in the second preparatory state;
    producing as another of the recognition signals a second recognition signal having a logical state "1" or "0", depending upon whether the second auxiliary value is greater or smaller than the second threshold value;
    producing a first control signal when there is formed the recognition-data word from grouping together of the logical state "1" for the first recognition signal and the logical state "0" for the second recognition signal;
    delivering said control signal to at least one computer in order to trigger thereat calculation of the erythrocyte concentration from the result of the particle count and a correlated coefficient;
    producing a second control signal when the recognition-data word consists of a composite of the logical state "1" for both recognition signals; and
    delivering said second control signal to at least one computer in order to obtain calculation of the leukocyte concentration from the result of the particle count and from a correlated coefficient and a calculation of the hemoglobin concentration from the result of the photometric measurement a correlated coefficient.

3. The method as defined in claim 1, for the analysis of blood in an analysis system, comprising the steps of:
    providing at least one measuring device for the analysis of particles suspended in the measuring liquid and with regard to their size classification and number per size classification;
    the measuring liquid essentially comprising an isotonic plasma replacement solution and a blood sample contained therein in one of two preparatory states, wherein of these two preparatory states the first constitutes higher dilution of the blood sample in the solution and the second a lower dilution of a plasma residue which has been separated from the blood sample;
    calculating the ratio of the result of the particle count in the size classification corresponding to the erythrocytes to the result of the particle count in the size classification corresponding to the thrombocytes;
    equating a first auxiliary value to said ratio and a second auxiliary value to the result of the particle count in the size classification corresponding to the erythrocytes;
    comparing the first auxiliary value with a correlated first threshold value which is predetermined in a range of 5% to 50% of the value of said ratio which is to be expected for a physiologically normal blood sample in the first preparatory state;

producing as one of the recognition signals a first recognition signal having a logical state "1" or "0", depending upon whether the first auxiliary value is larger or smaller than the first threshold value;

comparing the second auxiliary value with a correlated second threshold value which is predetermined in a range of 5% to 50% of the result of the particle count which is to be expected with a physiologically normal blood sample in the second preparatory state in the size classification corresponding to the erythrocytes;

producing as another of the recognition signals a second recognition signal whose logical state is "1" or "0", depending upon whether the second auxiliary value is greater or smaller than the second threshold value;

producing a first control signal when the recognition-data word contains the logical state "1" for the first recognition signal;

producing a second control signal when the recognition-data word is formed from grouping together the logical states "0" for both recognition signals;

triggering by means of each of these control signals in the computer calculation of the thrombocyte concentration from the result of the particle analysis in the size classification corresponding to the thrombocytes and from a correlated coefficient; and the first control signal is correlated to the coefficient corresponding to the higher dilution and the second control signal is correlated to the coefficient corresponding to the lower dilution.

4. The method as defined in claim 3, further including the steps of:

additionally providing the analysis system with a measuring device for measuring the conductivity of the measuring liquid;

comparing the results of the conductivity measurement with a correlated calibration-threshold value;

said calibration-threshold value being predetermined in the range of 5% to 50% of the result of the conductivity measurement which is to be expected with a pure carrier liquid;

producing a binary calibration signal having a logical state "1" or "0", depending upon whether the result of the conductivity measurement is greater or smaller than the calibration-threshold value;

grouping together the recognition signals and the calibration signal in a predetermined arrangement into an expanded recognition-data word;

comparing the recognition signals and the calibration signal with expanded preparation-data words which are predetermined for each of the possible preparatory states and with at least one predetermined calibration-data word corresponding to the pure carrier liquid;

producing a logical control signal characteristic of the calibration upon coincidence of the expanded recognition-data word with a calibration-data word;

delivering this control signal to the computer in order to trigger thereat a calibration operation;

calculating the sum of the result of the particle count in the size classification corresponding to the erythrocytes and the result of the particle count in the size classification corresponding to the thrombocytes;

equating a third auxiliary value to said sum;

comparing the third auxiliary value with a correlated third threshold value which is predetermined in a range of 5% to 50% of the result of the calculation of the aforementioned sum which is to be expected with a physiologically normal blood sample in the first preparatory state;

producing a third recognition signal whose logical state amounts to "1" or "0", depending upon whether the third auxiliary value is greater or smaller than the third threshold value.

5. The method as defined in claim 1, further including the steps of:

additionally providing the analysis system with a measuring device for measuring the conductivity of the measuring liquid;

comparing the results of the conductivity measurement with a correlated calibration-threshold value;

said calibration-threshold value being predetermined in the range of 5% to 50% of the result of the conductivity measurement which is to be expected with a pure carrier liquid;

producing a binary calibration signal having a logical state "1" or "0", depending upon whether the result of the conductivity measurement is greater or smaller than the calibration-threshold value;

grouping together the recognition signals and the calibration signal in a predetermined arrangement into an expanded recognition-data word;

comparing the recognition signals and the calibration signal with expanded preparation-data words which are predetermined for each of the possible preparatory states and with at least one predetermined calibration-data word corresponding to the pure carrier liquid;

producing a logical control signal characteristic of the calibration upon coincidence of the expanded recognition-data word with a calibration-data word; and delivering this control signal to the computer in order to trigger thereat a calibration operation.

* * * * *